(12) United States Patent
Zastawny et al.

(10) Patent No.: US 8,109,910 B2
(45) Date of Patent: Feb. 7, 2012

(54) FLIP-TOP DESIGN CANNULA

(75) Inventors: Mathieu Zastawny, Philadelphia, PA (US); Peter Byar, Willingboro, NY (US)

(73) Assignee: Tyco Healthcare Group LP, New Haven, CT (US)

( * ) Notice: Subject to any disclaimer, the term of this patent is extended or adjusted under 35 U.S.C. 154(b) by 263 days.

(21) Appl. No.: 12/357,647

(22) Filed: Jan. 22, 2009

(65) Prior Publication Data

US 2009/0209915 A1 Aug. 20, 2009

Related U.S. Application Data

(60) Provisional application No. 61/028,532, filed on Feb. 14, 2008.

(51) Int. Cl.
*A61M 5/178* (2006.01)
(52) U.S. Cl. ............... 604/167.02; 604/167.06; 604/256
(58) Field of Classification Search ......... 604/166.01–167.06, 174–175, 604/249, 259, 256; 215/211, 216, 224, 235, 215/242–243, 382–383, 385, 356
See application file for complete search history.

(56) References Cited

U.S. PATENT DOCUMENTS

| | | | |
|---|---|---|---|
| 4,634,421 A | 1/1987 | Hegemann | |
| 4,653,477 A | 3/1987 | Akui et al. | |
| 4,715,360 A | 12/1987 | Akui et al. | |
| 4,944,732 A | 7/1990 | Russo | |
| 5,197,955 A | 3/1993 | Stephens et al. | |
| 5,221,264 A | 6/1993 | Wilk et al. | |
| 5,242,412 A | 9/1993 | Blake, III | |
| 5,263,944 A | 11/1993 | Vidal et al. | |
| 5,300,036 A * | 4/1994 | Mueller et al. | 604/167.06 |
| 5,338,307 A | 8/1994 | Stephens et al. | |
| 5,413,561 A | 5/1995 | Fischell et al. | |
| 5,423,761 A | 6/1995 | Hein et al. | |
| 5,423,848 A | 6/1995 | Washizuka et al. | |
| 5,460,615 A | 10/1995 | Storz | |
| 5,512,053 A | 4/1996 | Pearson et al. | |
| 5,569,206 A | 10/1996 | Gorman, Jr. et al. | |
| 5,607,397 A | 3/1997 | Stephens et al. | |
| 5,624,410 A | 4/1997 | Tsukada et al. | |

(Continued)

FOREIGN PATENT DOCUMENTS

EP 0673626 A 9/1995

(Continued)

OTHER PUBLICATIONS

European Search Report dated Jun. 9, 2009 in co-pending EP application No. EP 09250327.5.

(Continued)

*Primary Examiner* — Nicholas Lucchesi
*Assistant Examiner* — Melissa A Snyder (57) ABSTRACT

There's provided a flip-top cannula assembly including a cannula having a cannula seal for receiving a range of surgical instruments having a first predetermined diameter and a reducer cap movably mounted on the cannula. The reducer cap includes a reducer seal having an opening which is substantially smaller than that of a cannula seal associated with the cannula for receiving a range of surgical instruments having a diameter smaller than that of the first predetermined diameter. In the disclosed embodiments, the reducer seal is movable from a closed position wherein the reducer seal overlies the cannula seal to effectively reduce the seal opening of the cannula to a closed position wherein the reducer seal is spaced apart from the cannula seal.

19 Claims, 10 Drawing Sheets

U.S. PATENT DOCUMENTS

| | | | |
|---|---|---|---|
| 5,657,963 A | 8/1997 | Hinchliffe et al. | |
| 5,752,938 A | 5/1998 | Flatland et al. | |
| 5,792,113 A | 8/1998 | Kramer et al. | |
| 5,843,040 A * | 12/1998 | Exline | 604/164.11 |
| 5,868,714 A | 2/1999 | Danks | |
| 6,017,359 A * | 1/2000 | Gershony et al. | 606/213 |
| 6,093,176 A | 7/2000 | Dennis | |
| 6,123,689 A | 9/2000 | To et al. | |
| 6,159,182 A | 12/2000 | Davis et al. | |
| 6,162,196 A | 12/2000 | Hart et al. | |
| 6,217,555 B1 | 4/2001 | Hart et al. | |
| 6,409,220 B1 | 6/2002 | Wing et al. | |
| 6,551,282 B1 | 4/2003 | Exline et al. | |
| 6,923,792 B2 | 8/2005 | Staid et al. | |
| 6,942,671 B1 | 9/2005 | Smith | |
| 6,945,983 B2 | 9/2005 | Dittrich et al. | |
| 7,169,130 B2 | 1/2007 | Exline et al. | |
| 2004/0006356 A1 | 1/2004 | Smith | |
| 2005/0070850 A1 | 3/2005 | Albrecht | |
| 2005/0070851 A1 | 3/2005 | Thompson et al. | |
| 2006/0135972 A1 | 6/2006 | Zeiner | |
| 2006/0135977 A1 | 6/2006 | Thompson et al. | |
| 2006/0135978 A1 | 6/2006 | Franer | |
| 2008/0091144 A1 * | 4/2008 | Moran et al. | 604/167.06 |
| 2009/0036745 A1 * | 2/2009 | Bonadio et al. | 600/208 |

FOREIGN PATENT DOCUMENTS

| | | |
|---|---|---|
| EP | 1716813 A | 11/2006 |
| WO | WO2008/023200 A | 2/2008 |
| WO | WO 2008/023200 A | 2/2008 |

OTHER PUBLICATIONS

European Search Report for corresponding EP09250327 date of mailing is Jun. 9, 2009 (4 pages).

* cited by examiner

FLIP-TOP DESIGN CANNULA

CROSS REFERENCE TO RELATED APPLICATION

The present application claims the benefit of and priority to U.S. Provisional Application Ser. No. 61/028,532 filed on Feb. 14, 2008, the entire contents of which are incorporated herein by reference.

BACKGROUND

1. Technical Field

The present disclosure relates to flip-top style adapters for use with a cannula. More particularly, the present disclosure relates to cannulas having flip-top adapters for reducing the inlet opening of the cannula to accommodate smaller diameter instruments.

2. Background of Related Art

In various surgical procedures it is often desirable to access a body cavity with minimal trauma to a patient. These type of surgeries are often termed endoscopic or laparoscopic and involve forming one or more small incisions in the body of the patient and utilizing a cannula to provide access to the body cavity for various surgical instruments. The cannula is also used to provide a source of insufflation fluid to insufflate the body cavity thereby creating a working space within the body cavity.

Cannulas typically include a cannula body defining an inner chamber and an elongate tubular member extending distally from the cannula body which is inserted through the incision to provide a pathway for the surgical instrument. A seal having an opening for receipt of the surgical instrument is provided at the proximal end of the cannula body to prevent escape of the insufflation gases.

The opening of the cannula seal has a predetermined diameter which is configured to correspond to the diameters of a particular range of surgical instruments. Often however, it is necessary to utilize surgical instruments having a smaller diameter which is not sufficiently large to properly seal within the opening of the cannula seal. This may result in escape of insufflation fluids from the body cavity thereby making various surgeries more difficult.

Thus, it is desirable to provide a cannula assembly which includes a reducer seal having a smaller diameter opening than the cannula seal to allow for the use of smaller diameter surgical instruments. It is further desirable to provide a cannula assembly which includes a reducer seal attached to the cannula assembly and selectively positionable adjacent the cannula seal to effectively reduce the diameter of the cannula seal.

SUMMARY

There is disclosed a flip-top cannula including a cannula having a cannula body defining an inner chamber, an elongate tubular member extending distally from the cannula body and a cannula seal positioned on a proximal end of the cannula body. The cannula includes a seal having an opening of a first predetermined diameter for receipt of a first surgical instrument. The flip-top cannula additionally includes a reducer cap movably mounted on the cannula body and including a reducer seal defining a bore having a second predetermined diameter for receipt of a second surgical instrument, the second predetermined diameter being less than the first predetermined diameter. The reducer cap is movable from an open position spacing the reducer seal from the cannula seal to a closed position wherein the reducer seal overlies the cannula seal.

The reducer cap is pivotally mounted to the cannula body. In one embodiment, the cannula body includes at least one pivot pin and the reducer cap is pivotally mounted on the at least one pin. In a specific embodiment, the cannula body includes a pair of pins and the reducer cap includes a back span defining a pair of legs extending distally from the back span, the legs being pivotally mounted to the pair of pins. The back span includes a center portion containing the reducer seal.

There is also disclosed a flip-top cannula including a cannula having a cannula body defining an inner chamber, an elongate tubular member extending distally from the cannula body and a cannula seal positioned on a proximal end of the cannula body. The cannula seal has an opening of a first predetermined diameter for receipt of a first surgical instrument. The flip-top cannula further includes a reducer cap including a reducer seal defining a bore having a second predetermined diameter for receipt of a second surgical instrument, the second predetermined diameter being less than the first predetermined diameter. The reducer cap includes a first portion connected to the cannula body, a second portion movably mounted relative to the first portion and a flexible hinge connecting the first and second portions. The second portion is movable from an open position spacing the reducer seal from the cannula seal to a closed position wherein the reducer seal overlies the cannula seal.

In one embodiment, the living hinge is integral with the first and second portions. In a specific embodiment, the living hinge is formed of an elastomeric material. In a yet more specific embodiment, the living hinge is molded to hold the second portion in an open position of approximately 135° relative to the first portion when the living hinge is in an unstressed condition.

In one embodiment, the first portion circumferentially surrounds the cannula body such that the reducer cap is rotatable around at least a portion of the cannula body.

In another embodiment, the second portion includes a concave portion surrounding the reducer seal such that the concave portion guides a surgical instrument towards the reducer seal.

In a further embodiment, the cannula body includes a recess and the reducer cap includes an inwardly directed lip engageable with the recess to hold the reducer cap in the closed position.

In a specific embodiment, the first portion includes a plurality of nubs to facilitate grasping the cannula.

In another specific embodiment, the cannula body includes a suture flange defining a suture hole for receipt of suture material to secure the cannula relative to tissue.

In yet a further specific, embodiment the cannula body includes at least one projection having a groove for receipt of suture material.

There is also disclosed a flip-top cannula including a cannula having a cannula body defining an inner chamber, an elongate tubular member extending distally from the cannula body and a cannula seal positioned on a proximal end of the cannula body. The cannula seal has an opening of a first predetermined diameter for receipt of a first surgical instrument. The flip-top cannula additionally includes a reducer cap formed integrally with the cannula body and including a reducer seal defining a bore having a second predetermined diameter for receipt of a second surgical instrument, the second predetermined diameter being less than the first predetermined diameter.

In a specific embodiment, the flip-top cannula further includes a flexible, living hinge integrally formed between the cannula and the reducer cap.

In another specific embodiment, the cannula body includes a channel having at least one suture hole, the channel directing a surgical needle having suture material towards the at least one suture hole. In a more specific embodiment the reducer cap is asymmetric.

DESCRIPTION OF THE DRAWINGS

Various embodiments of the presently disclosed cannulas are disclosed herein with reference to the drawings, wherein.

DETAILED DESCRIPTION OF EMBODIMENTS

Embodiments of the presently disclosed cannulas having flip-top type reducer caps will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
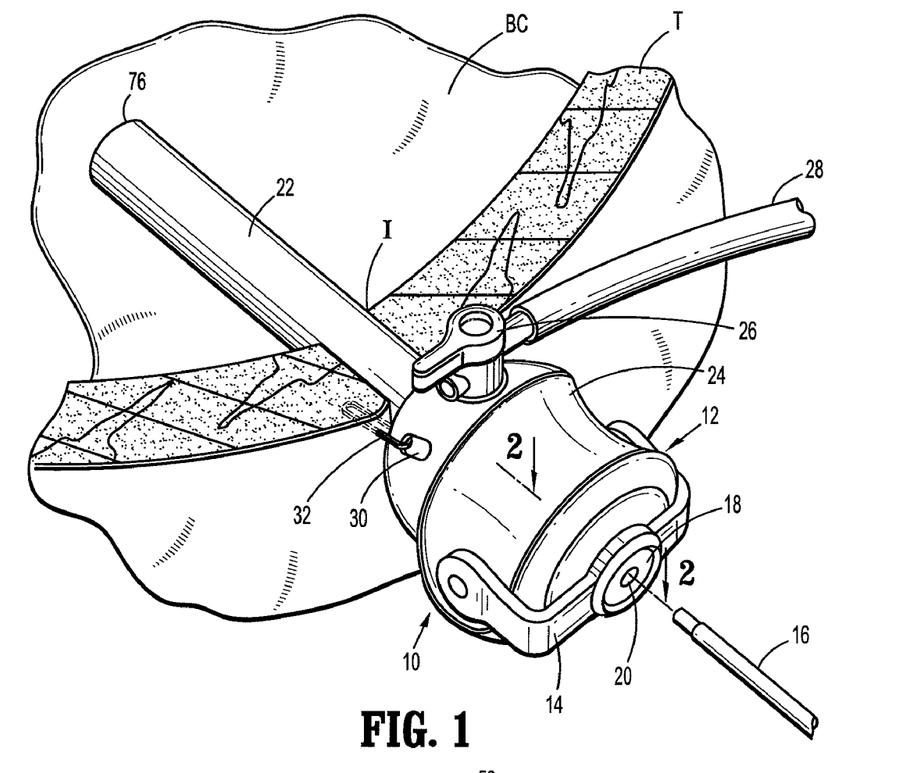
FIG. 1 is a perspective view of one embodiment of a cannula incorporating a bail, flip-top reducer cap and illustrating the cannula inserted into tissue.

Referring initially to FIG. 1, there is disclosed a bail type, flip-top cannula 10 generally including a cannula 12 and a bail type reducer cap 14 movably mounted on cannula 12. Reducer cap 14 is provided to accommodate a first surgical instrument 16 having a predetermined diameter typically smaller than that of other surgical instruments used through cannula 12. Reducer cap 14 incorporates a reducer seal 18 having reducer bore 20 configured to receive first surgical instrument 16 as described in more detail hereinbelow.

Cannula 14 is of a type typically known in the art and generally includes an elongate tubular member 22 extending distally from a cannula body 24. Elongate tubular member 22 is provided to extend through an incision I in a tissue T in order to provide access a body cavity BC for surgical instruments such as, for example, surgical instrument 16. Cannula body 24 includes a valve 26 for receipt of a source of insufflation fluid 28. Cannula body 24 also includes one or more suture holes 30. As shown, suture holes 30 are provided to receive sutures 32 to secure cannula 12 to tissue T.

Figure 2:
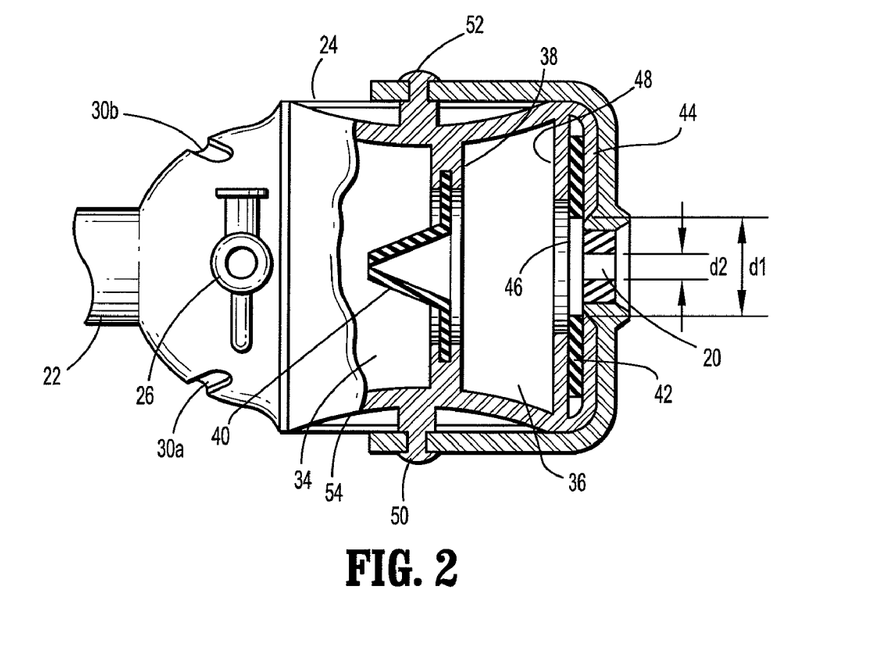
FIG. 2 is a side view, partially shown in section, taken along line 2-2 of FIG. 1.

Referring now to FIG. 2, as noted above, cannula 12 is generally constructed as a typical cannula and includes a first inner chamber 34 in fluid communication with elongate tubular member 22 and a second inner chamber 36. A flange 38 supports a duck bill type valve 40 positioned between first and second inner chambers 34 and 36. Duck bill valve 40 is provided to isolate first inner chamber 34 from second inner chamber 36 during insufflation of body cavity BC, as well as, seal around surgical instrument 16 when inserted therethrough. Cannula body 24 is also provided with a cannula seal 42 located on a proximal end 44 of cannula body 24. Cannula seal 42 includes a seal opening 46 having a predetermined diameter d1 to accommodate a surgical instrument having a different diameter than that of surgical instrument 16. Diameter d1 of seal opening 46 is larger than a diameter d2 of reducer bore 20, of reducer seal 18, in order to accommodate surgical instruments having a diameter larger than that of surgical instrument 16 as described in more detail hereinbelow. Cannula seal 42 is supported within a flange 48 provided in proximal end 44 of cannula body 24.

Figure 3:
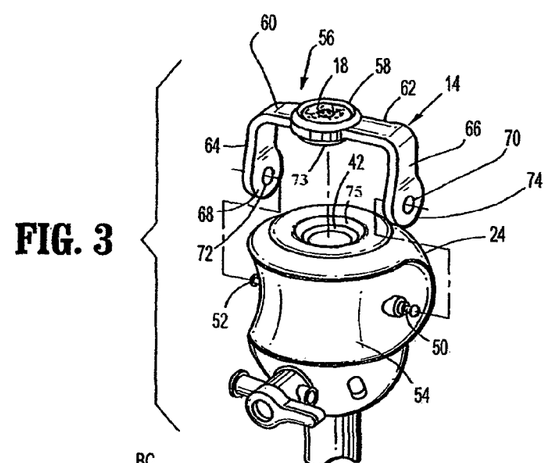
FIG. 3 is a perspective view of the embodiment of FIG. 1 with the reducer cap separated from a cannula body.

Referring now to FIGS. 2 and 3, and as noted hereinabove, reducer cap 14 is movably mounted on cannula 12. Specifically, reducer cap 14 is pivotally mounted on pivot pins 50 and 52 extending from a recessed area 54 on cannula body 24. Recessed area 54 extends partially around cannula body 24 and is provided to receive reducer cap 14 such that reducer cap 14 is less obtrusive when moved to the open position away from cannula seal 42.

Referring specifically to FIG. 3, the details of reducer cap 14 will now be described. As noted hereinabove, reducer cap 14 is of a generally bail shape and generally includes a back span 56 having a circular central portion 58. Circular central portion 58 is provided to support the reducer seal 18 centrally over cannula seal 42 when reducer cap 14 is in the closed position. A pair of arms 60 and 62 extend laterally away from central circular portion 58. A pair of distally extending legs 64 and 66 extend distally from arms 60 and 62, respectively, and are provided with pivot holes 68 and 70 at distal ends 72 and 74, respectively. Circular central portion 58 is provided with a downwardly extending lip 73 which is configured to seal within a shallow region 75, provided adjacent cannula seal 42, when reducer cap 14 is in the closed position. While not specifically shown, legs 64 and 66 may be oriented offset of a longitudinal axis of cannula 12 to facilitate pivoting reducer cap 14.

Preferably, reducer cap 14 is formed of a substantially elastomeric material such that reducer cap 14 can be stretched up and away from proximal end 44 of cannula body 24 when reducer cap 14 is moved from the closed to the open position. Additionally, the elastomeric nature of reducer cap 14 allows reducer cap 14 to lie substantially within recessed area 54 in cannula body 24 thus allowing reducer cap 14 to be relatively unobtrusive when in the open position.

Referring for the moment back to FIG. 1, in use, cannula 12 is positioned against tissue T and is manipulated such that elongate tubular member 22 is inserted through incision I to position an open distal end 76 of elongate tubular member 22 within body cavity BC. As shown, reducer cap 14 is in the closed position with reducer seal 18 positioned over cannula seal 42 (see FIG. 2). In this position, the smaller diameter reducer bore 20 in reducer seal 18 is in a position to receive first surgical instrument 16. Since the diameter of first surgical instrument 16 is substantially similar to smaller diameter d2 of reducer bore 20 surgical instrument 16 seals within reducer seal 18. As noted hereinabove, body cavity BC can be insufflated by opening valve 26 and allowing insufflation gases to pass through source of insufflation fluids 28, into first inner chamber 34 and through elongate tubular member 22 into body cavity BC. In the absence of surgical instrument 16, duck bill valve 40 seals against the escape of insufflation gases out of cannula body 24. A series of surgical procedures can now be performed within body cavity by first surgical instrument 16.

Figure 4:
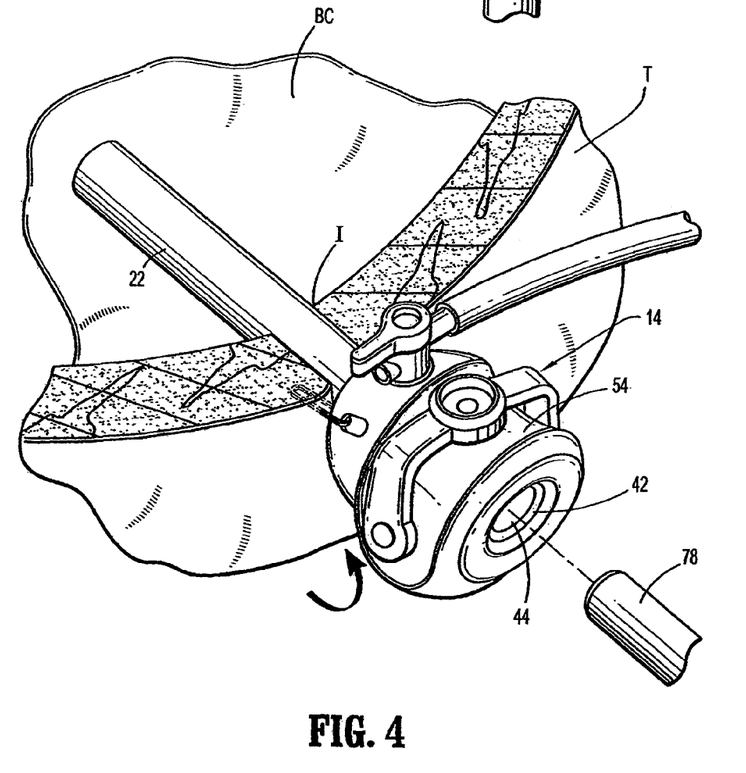
FIG. 4 is a perspective view similar to FIG. 1 with the reducer cap pivoted out of alignment with a seal of the cannula.

Referring now to FIG. 4, should a larger diameter surgical instrument, such as, for example, second surgical instrument 78, be needed to continue performing surgical operations within body cavity BC, reducer cap 14 can be pivoted from the open position to the closed position wherein reducer cap 14 lies substantially adjacent reduced area 54 of cannula body 24. In this condition, cannula seal 42 having the larger diameter seal opening 46 is available to receive larger diameter second surgical instrument 78 therethrough. As with first surgical instrument 16 hereinabove, second surgical instrument 78 passes through duck bill valve 40 and elongate tubular member 22 to perform further surgical operations within body cavity BC.

Figure 5:
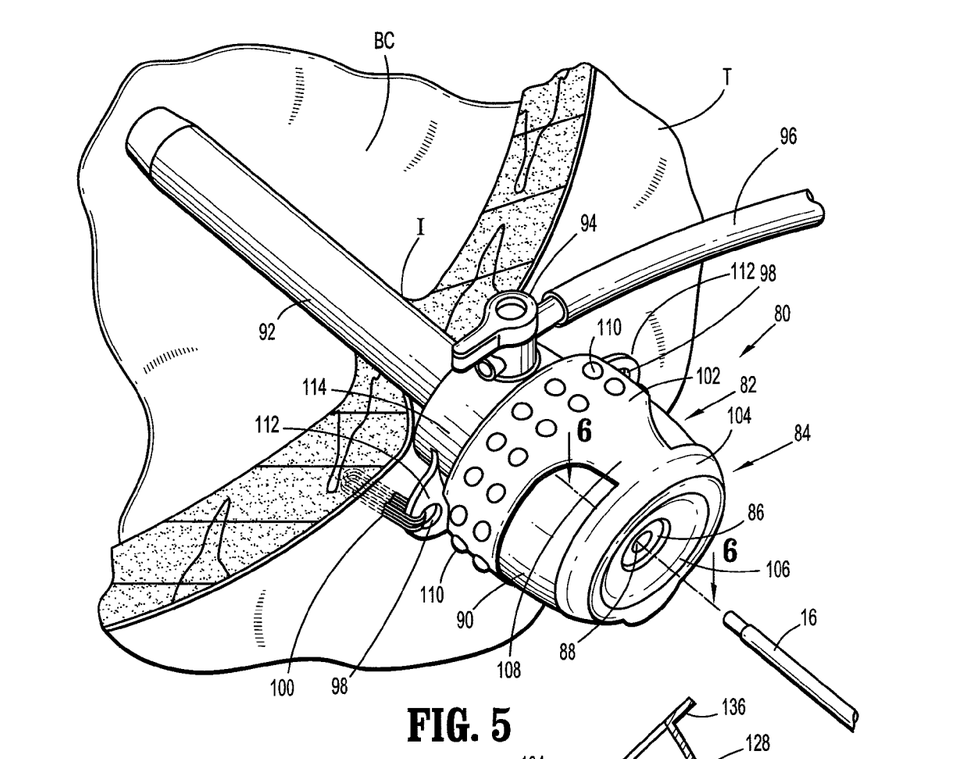
FIG. 5 is a perspective view of an alternative embodiment of a cannula incorporating an elastomeric, flip-top reducer cap.

Referring now to FIG. 5, there is disclosed an elastomeric, flip-top cannula 80 which generally includes a cannula 82 and an elastomeric reducer cap 84 movably mounted to cannula 82. Reducer cap 84 includes a reducer seal 86 having a reducer bore 88 which is configured to seal about a surgical instrument having a predetermined diameter such as, for example, first surgical instrument 16.

Cannula 82 generally includes a cannula body 90 having an elongate tubular member 92 extending distally from cannula body 90. Elongate tubular member 92 is configured to pass through an incision I in tissue T and into body cavity BC to provide access for first surgical instrument 16 into body cavity BC to perform surgical procedures therein. Similar to cannula 12 describe hereinabove, cannula body 90 is provided with a valve 94 which is connected to a source of insufflation fluid 96. Cannula body 90 additionally includes one or more suture holes 98 which are configured to receive sutures 100 and secure cannula 82 to tissue T.

Elastomeric reducer cap 84 is formed of a flexible, elastomeric material and generally includes a first, substantially circumferential portion 102 and a second, substantially circumferential portion 104. Second circumferential portion 104 supports reducer seal 86. A concave portion 106 is formed within second circumferential portion 104 and substantially surrounds reducer seal 86 so as to facilitate guiding first surgical instrument 16 toward reducer bore 88 in reducer seal 86. First and second substantially circumferential portions 102 and 104 are connected by a flexible or living hinge 108 which allows second circumferential portion 104 to be movable relative to cannula body 90. Second circumferential portion 104 is movable between a closed position placing reducer seal 86 in a position to receive first surgical instrument 16 to an open position such that second circumferential portion 104 is moved or pivoted out of a position to receive first surgical instrument 16. Living hinge 108 is molded such that in an open, unstressed position second circumferential portion 104 is held at an angle of approximately 135° relative to first circumferential portion 102. A plurality of nubs 110 are provided on first circumferential portion 102 to facilitate grasping cannula 82. Additionally, nubs 110 may allow reducer cap 84 to be rotated about cannula body 90 such that second circumferential portion 104 may be positioned out of the way of valve 94 when in the open position.

In this embodiment, suture holes 98 are formed through suture flanges 112 extending from a distal end 114 of cannula body 90. Suture flanges 112 may be affixed to distal end 114 or may be formed integrally therewith.

Figures 6, 7:
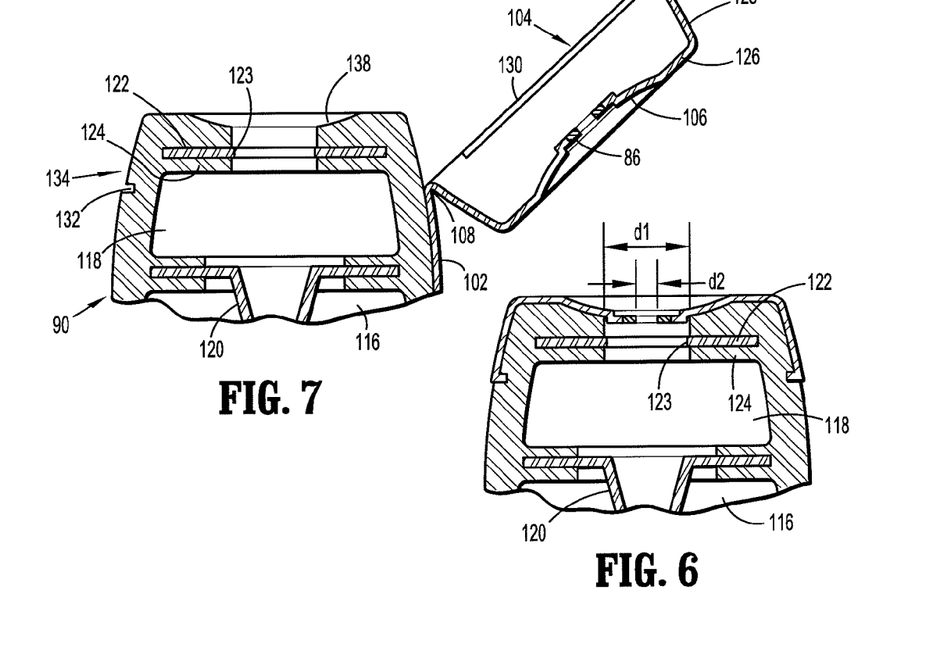
FIG. 6 is a side sectional view taken along line 6-6 of FIG. 5.
FIG. 7 is a side sectional view similar to FIG. 6 with the reducer cap pivoted out of alignment with a seal of the cannula.

Referring now to FIGS. 6 and 7, similar to cannula body 24 described hereinabove, cannula body 90 includes a first inner chamber 116 and a second inner chamber 118 separated by a duck bill valve 120. A cannula seal 122 is supported within cannula body 90 by a flange 124 and defines a seal opening 123 having a predetermined diameter d1 (FIG. 6) for receipt of a surgical instrument having a larger diameter that surgical instrument 16.

Figure 8:
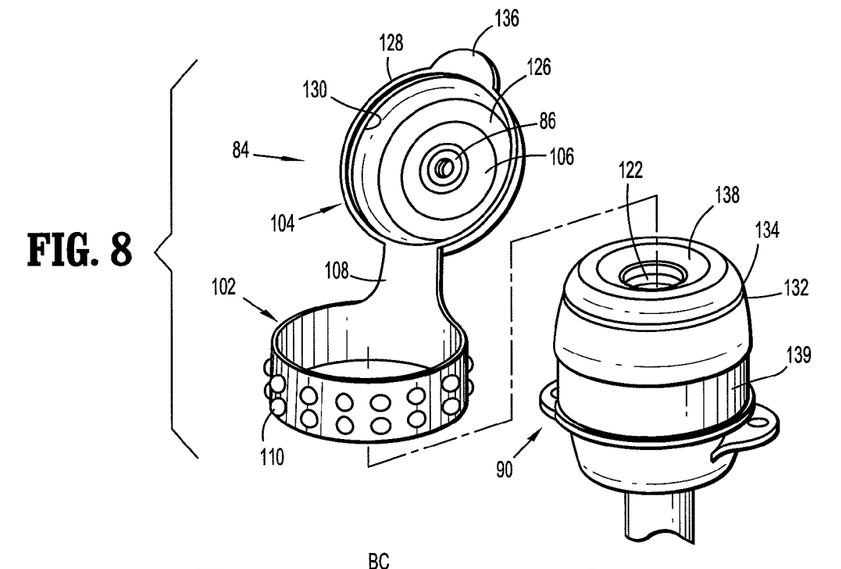
FIG. 8 is a perspective view of the embodiment of FIG. 5 with the reducer cap removed from a cannula body.

As best seen in FIGS. 7 and 8, second circumferential portion 104 of reducer cap 84 generally includes a top surface 126 and a circumferential downwardly extending side surface 128. In order to secure second circumferential portion 104 against cannula body 90, side surface 128 is provided with an inner protrusion 130 which is configured to engage an indentation 132 formed in proximal end 134 of cannula body 90. A tab 136 may be provided on side surface 128 to facilitate disengaging inner protrusion 130 from indentation 132.

A concave portion 138 adjacent cannula seal 122 in cannula body 90 is provided to seal against concave portion 106 of second circumferential portion 104 of reducer cap 84 when reducer cap 84 is in the closed position.

Referring for a moment to FIG. 7, first circumferential portion 102 of reducer cap 84 may be secured to cannula fighting 90 by gluing, welding, etc. Alternatively, referring to FIG. 8, first circumferential portion 102 may engage a depressed region 139 in cannula body 90. In this configuration, reducer cap 84 may be rotatable within depressed region 139 so as to rotate reducer cap 84 relative to cannula body 90. This allows the surgeon to orient second circumferential portion 104 away from valve 94 when second circumferential portion 104 of reducer cap 84 is in the open position spaced away from cannula seal 122.

Referring back to FIG. 5, in use, cannula 82 is manipulated such that elongate tubular member 92 is positioned through incision I in tissue T so as to locate elongate tubular member 92 within body cavity BC. Thereafter, a valve 94 may be opened to receive source of insufflation fluid 96 in order to insufflated body cavity BC. When using first surgical instrument 16, second circumferential portion 104 of reducer cap 84 is in the closed position placing reducer seal 86 in a position to receive surgical instrument 16. Thereafter, surgical instrument 16 is inserted through reducer bore 88 and reduces seal 86 to position surgical instrument 16 within body cavity BC. Surgical procedures may now be performed within body cavity BC with surgical instrument 16.

Figure 9:
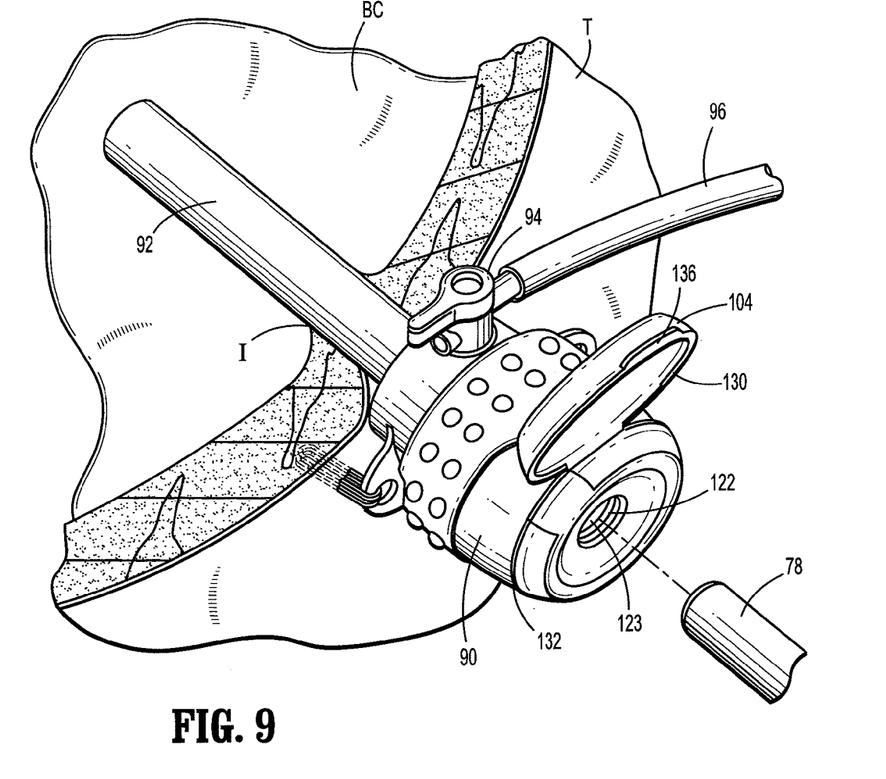
FIG. 9 is a perspective view similar to FIG. 5 with the reducer cap pivoted out of position relative to the seal.

Referring now to FIG. 9, when the surgical procedures requires the use of a second surgical instrument 78 having a diameter greater than that of first surgical instrument 16, second circumferential portion 104 of reducer cap 84 may be moved to the open position to expose cannula seal 122. Specifically, tab 136 on second circumferential portion 104 is manipulated to disengage inner protrusion 130 from indentation 132 formed in cannula body 90. Second surgical instrument 78 is advanced towards cannula body 90 such that second surgical instrument 78 is guided towards cannula seal 122 by concave portion 138 formed in cannula body 90. Second surgical instrument 78 is advanced through seal opening 123, and thus through elongate tubular member 92, to position second surgical instrument 78 within body cavity BC. Further surgical procedures may now be performed within body cavity BC by surgical instrument 78.

Thus, elastomeric flip top cannula 80, including concave portion 106 in second circumferential portion 104 and concave portion 138 formed in cannula body 90, provides the advantage of improving guidance of a surgical instrument towards reducer seal 86 and cannula seal 122, respectively.

Figure 10:
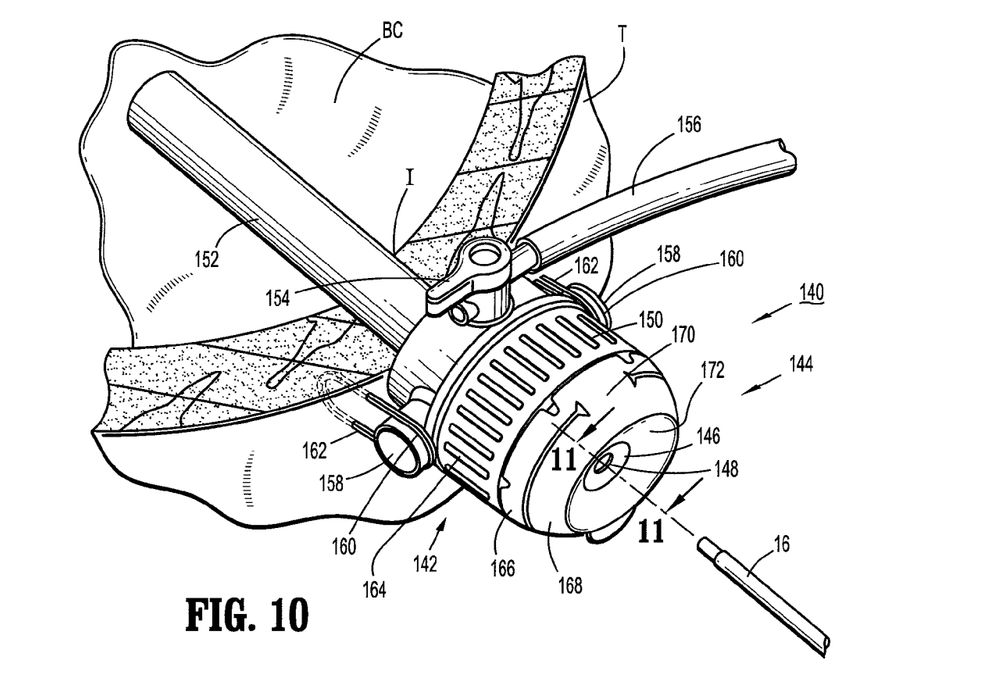
FIG. 10 is a perspective view of another alternative of a cannula incorporating a living-hinge, flip top reducer cap.

Referring now to FIG. 10, there is disclosed a living hinge, flip-top cannula 140 for use in receiving various diameter surgical instruments to perform surgical procedures within a body cavity BC. Living hinge, flip-top cannula 140 generally includes a cannula 142 and a living hinge reducer cap 144 movably mounted to cannula 142. Reducer cap 144 includes a reducer seal 146 having a reducer bore 148 for receipt of a relatively small diameter surgical instrument, such as, for example, first surgical instrument 16.

Similar to the cannulas described hereinabove, cannula 142 generally includes a cannula body 150 and an elongate tubular member 152 extending distally from cannula body 150. A valve 154 is provided on cannula body 150 and is engageable with a source of insufflation fluid 156 so as to supply insufflation fluid 156 to body cavity BC. Cannula body 150 is also provided with one or more projections 158 extending radically outward from cannula body 150. Projections 158 include suture grooves 160 extending at least partially around projections 158. Suture grooves 160 allow a single wrap of sutures, such as, for example sutures 162, to be utilized to secure cannula 142 to tissue T. A plurality of ribs 164 are provided circumferentially about cannula body 150 to facilitate manipulation of cannula 142.

Reducer cap 144 includes a first circumferential portion 166 and a second circumferential portion 168. First and second circumferential portions 166 and 168, respectively, are interconnected by a living hinge 170. As noted hereinabove, reducer cap 144 is formed of a flexible, elastomeric material. Living hinge 170 is molded to hold first circumferential portion 166 at an angle of approximately 150° relative to second circumferential portion 168 when first circumferential portion 166 is in the unstressed or disconnected conditioned from cannula body 150. Second circumferential portion 168 includes reducer seal 146 and a concave portion 172 which is configured to guide a surgical instrument, such as, for example, surgical instrument 16 toward reducer bore 148 in reducer seal 146.

Figure 11:
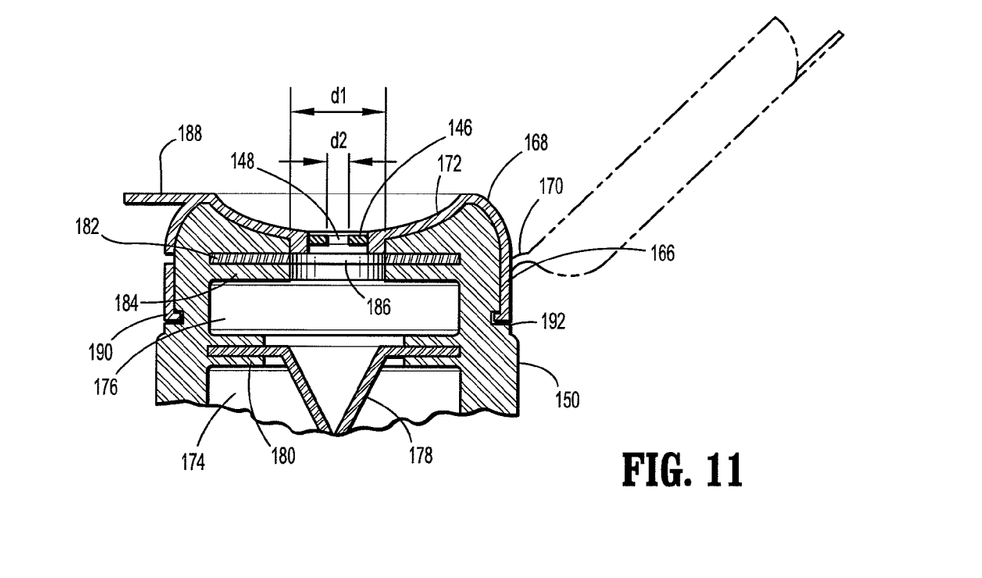
FIG. 11 is a side sectional view taken along line 11-11 of FIG. 10.

Referring now to FIG. 11, cannula body 150 includes a first inner chamber 174 and a second inner chamber 176. First and second inner chambers 174 and 176 respectively, are separated by a duckbill valve 178 which is supported within a flange 180 in cannula body 150. Cannula body 150 additionally includes a cannula seal 182 supported within a flange 184 on cannula body 150. Cannula seal 182 defines a seal opening 186 having a predetermined diameter d1 for receipt of surgical instruments having a diameter larger than that of surgical instrument 16. As shown, reducer bore 148 of reducer seal 146 as a predetermined diameter d2 which is less than that of diameter d1 of seal opening 186 of cannula seal 182.

Second circumferential portion 168 is provided with a tab 188 to facilitate moving second circumferential portion 168 from the closed or stressed condition wherein reducer seal 146 overlies cannula seal 182 to an open or unstressed position wherein reducer seal 146 is spaced away from cannula body 150 to allow surgical instruments to be inserted through cannula seal 182. As noted hereinabove, in the unstressed condition, second circumferential portion 168 is held at an angle of approximately 135° relative to first circumferential portion 166 and cannula body 150.

Figure 12:
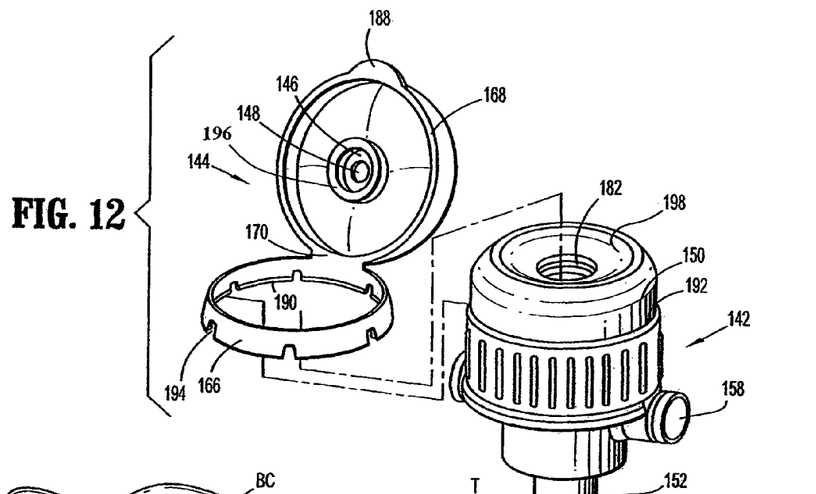
FIG. 12 is a perspective view of the embodiment of FIG. 10 with the reducer cap separated from a cannula body.

Referring now to FIGS. 11 and 12, first circumferential portion 166 is provided with an inner lip 190 which is configured to engage a hollow 192 formed in cannula body 150. Cut outs 194 provided in first circumferential portion 166 enable first circumferential portion 166 to be movable relative to cannula body 150. Specifically, first circumferential portion 166, and thus living hinge reducer cap 144, are rotatably mounted on cannula body 150.

Referring specifically to FIG. 12, second circumferential portion 168 is provided with a downward projection 196 surrounding reducer seal 146. Downward projection 196 seals against cannula seal 182 when second circumferential portion 168 is in the closed position. Cannula body 150 includes a concave portion 198 surrounding cannula seal 182. Concave portion 198 assists in guiding a surgical instrument towards cannula seal 182 when second circumferential portion 168 of reducer cap 144 is in the open or unstressed condition.

Referring back to FIG. 10, in use, living hinge flip-top cannula 140 is manipulated so as to insert elongate tubular member 152 through incision I in tissue T to position elongate tubular member 152 within body cavity BC. Sutures 162 are threaded around grooves 160 in projections 158 and used to secure elastomeric flip top cannula 80 to tissue T. Thereafter a valve 154 is opened to supply source of inflation fluid 156 into body cavity BC. Where a surgical instrument, such as surgical instrument 16 having a relatively small diameter is desired to be used, second circumferential portion 168 of reducer cap 144 is in the closed the position relative to first circumferential portion 166. Surgical instrument 16 is inserted through reducer opening 148 in reducer seal 146 and the desired surgical procedure is performed within body cavity BC.

Figure 13:
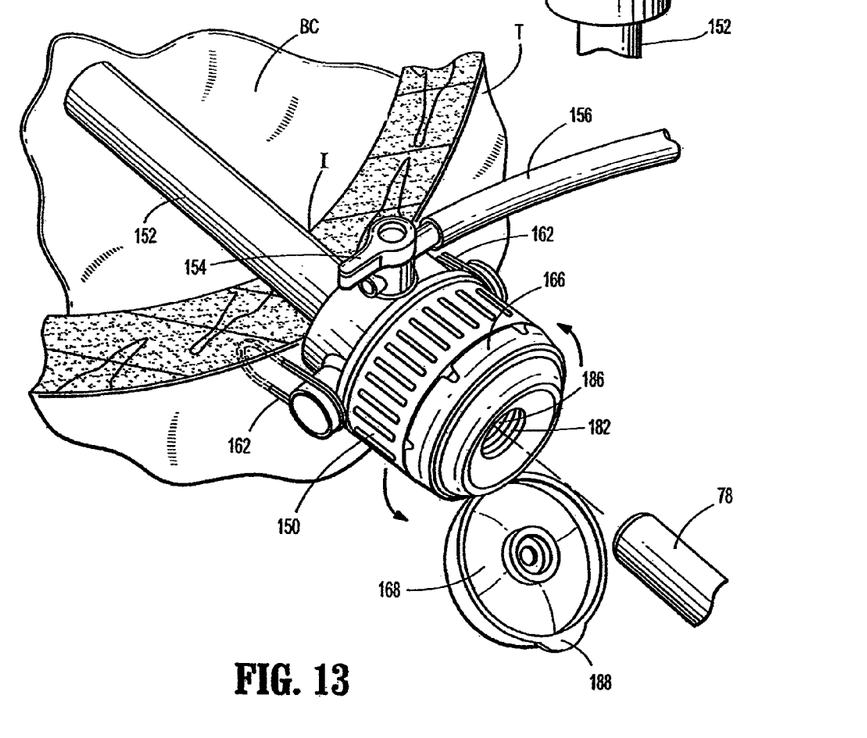
FIG. 13 is a perspective view similar to FIG. 10 with the reducer cap pivoted out of alignment relative to a seal of the cannula.

Referring now to FIG. 13, where a larger diameter surgical instrument, such as, for example surgical instrument 78, is desired to be used, second circumferential portion 168 is moved to the open or unstressed condition relative to first circumferential portion 166 of reducer cap 144. As noted hereinabove this is facilitated by the provision of tab 188 on second circumferential portion 168. It should be noted that reducer cap 144 may be rotated relative to cannula body 150 so as to position second circumferential portion 168 away from valve 154 to facilitate operation a valve 154. Second surgical instrument 78 is inserted through cannula opening 186 in cannula seal 182 and is used to perform additional surgical procedures within body cavity BC.

Thus, it can be seen that living hinge flip-top cannula 140 provides the advantages of having a reducer cap 144 that is rotatable relative to cannula body 150 to facilitate operation of valve 154, as well, as facilitating application of sutures 162 about projections 158 and through tissue T.

Figure 14:
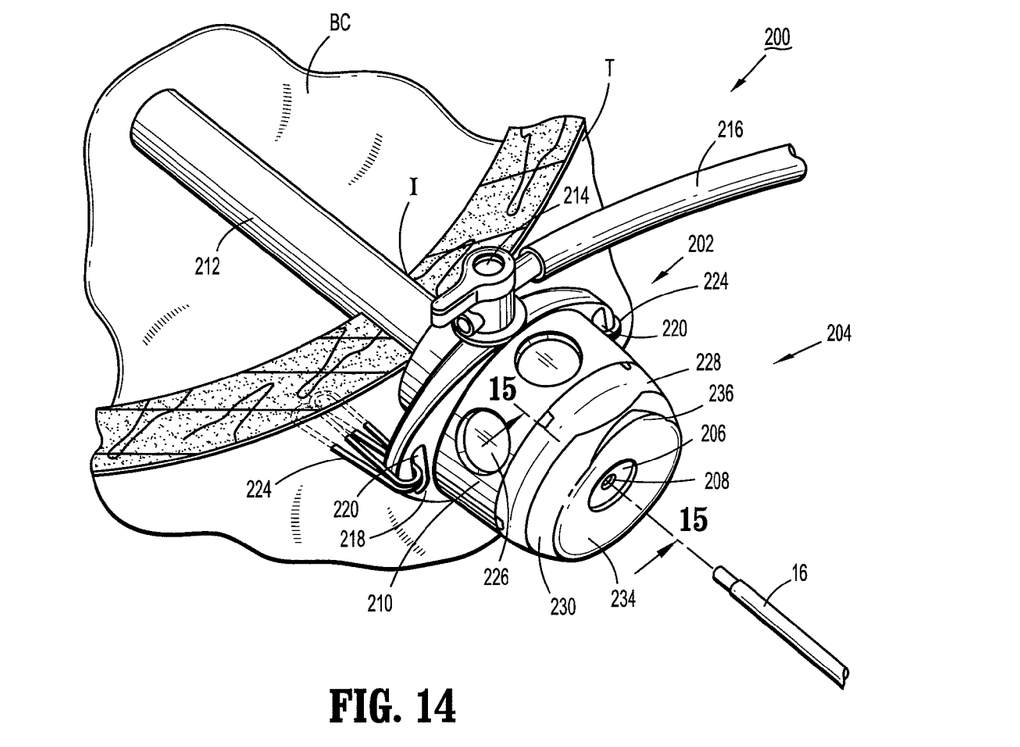
FIG. 14 is a perspective view of still another embodiment of a cannula incorporating a restyled, flip-top reducer cap.

Referring now to FIGS. 14-17, and initially with regard to FIG. 14, there is disclosed a restyled, flip-top cannula 200 for use with various diameter surgical instruments. Restyled, flip-top cannula 200 generally includes a cannula 202 and a restyled reducer cap 204. Reducer cap 204 includes a reducer seal 206 having a reducer bore 208. Cannula 202 includes a cannula body 210 having an elongate tubular member 212 extending distally there from. A valve 214 is provided on cannula body 210 and is connected to a source of insufflation fluid 216. A suture flange 218 is provided about cannula body 210 and is provided with one or more suture holes 220. Sutures 224 are provided to pass through suture holes 220 and secure restyled flip-top cannula 200 to tissue T. A plurality of depressions 226 are provided about cannula body 210 to facilitate manipulation of restyled flip-top cannula 200 through tissue T.

Reducer cap 204 includes a first circumferential portion 228 and a second circumferential portion 230. First and second circumferential portion stood 28, 230, respectively, are interconnected by a hinge 232. Hinge 232 may be integral with first and second circumferential portions 228, 230, respectively, or may be provided as a separate member. Reducer cap 204 is formed from elastomeric material and hinge 232 is molded such that in an unstressed condition second circumferential portion 230 is maintained at an angle of approximately 135° relative to first circumferential portion 228. Second circumferential portion 230 is provided with a concave portion 234 adjacent reducer seal 206 to facilitate guiding instruments towards reducer bore 208 in reducer seal 206. A protrusion 236 is provided on second circumferential portion 230 to facilitate moving second circumferential portion 230 from a closed position adjacent first circumferential portion 228 to an open or unstressed position spaced apart from first circumferential portion 228.

Figure 15:
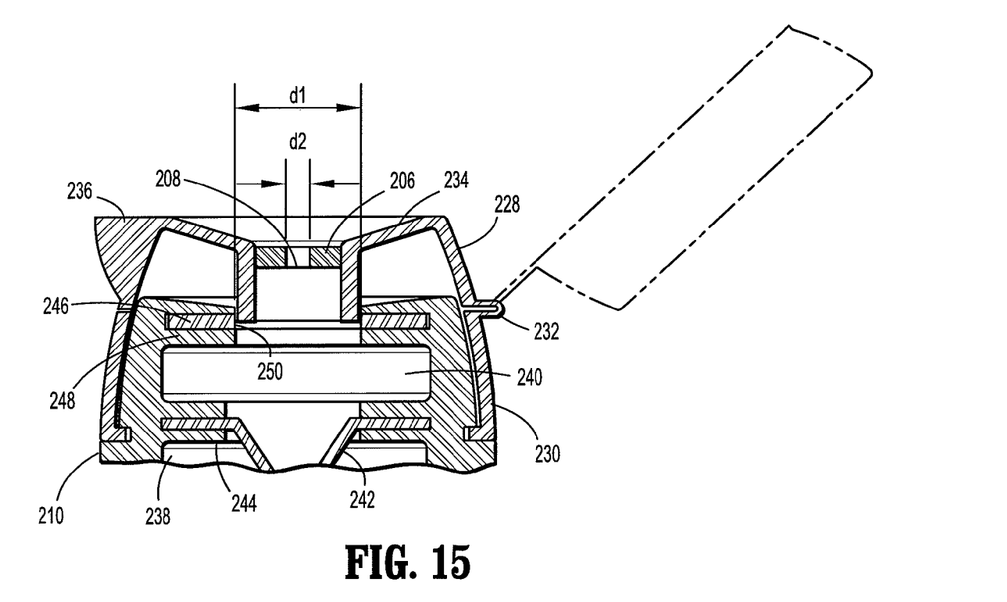
FIG. 15 is a side sectional view taken along line 15-15 of FIG. 14.

Referring now to FIG. 15, cannula body 210 includes a first inner chamber 238 and a second inner chamber 240. First and second inner chambers 238 and 240 are separated by a duckbill valve 242 supported within a flange 244 formed within cannula body 210. Cannula body 210 further includes a cannula seal 246 supported within a flange 248 formed in cannula body 210. Cannula seal 246 defines a seal opening 250 having a predetermined diameter d1 for receipt of surgical instruments having a diameter greater than that of surgical instrument 16.

Figure 16:
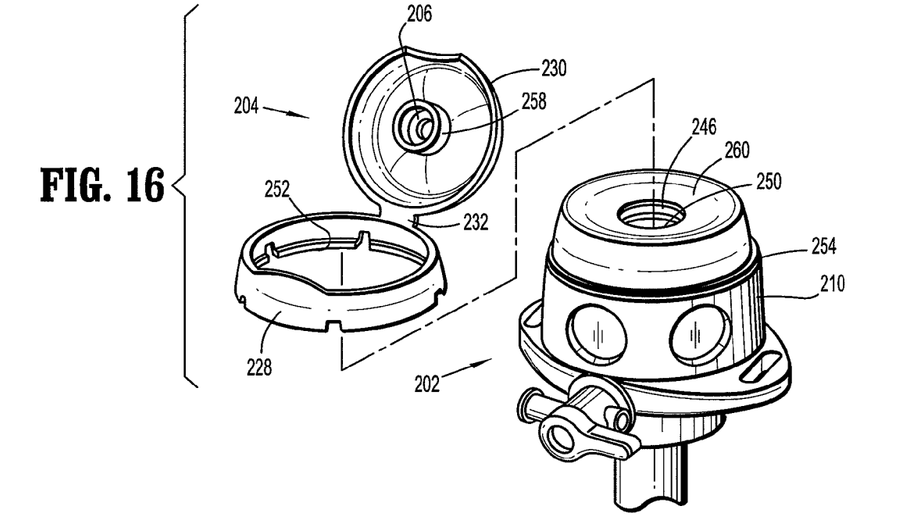
FIG. 16 is a perspective view of the embodiment of FIG. 14 with the reducer cap separated from a cannula body.

Referring to FIGS. 15 and 16, first circumferential portion 228 is provided with an inner tooth 252 which is configured to engage a cavity 254 formed in cannula body 210. Cut outs 256 formed in first circumferential portion 228 allow first circumferential portion 228 to engage cannula body 210 in a manner which allows reducer 204 to be rotated relative to cannula body 210. Similar to those embodiments described hereinabove, second circumferential portion 230 is provided with a downward projection 258 surrounding reducer seal 206 which allows second circumferential portion 232 seal against cannula body 210 and thus against cannula seal 246 when second circumferential portion 230 is in a close position relative to first circumferential portion 228. As shown, cannula body 210 additionally includes a concave portion 260 which is provided to guide surgical instruments towards seal opening 250 in cannula seal 246.

Referring now to FIG. 14, in use, restyled flip-top cannula 200 is manipulated to insert elongate tubular member 212 through incision I in tissue T so as to position elongate tubular member 212 within body cavity BC. As noted hereinabove, sutures 224 are passed through suture holes 220 in suture flange 218 to secure restyled flip top cannula 200 to tissue T. thereafter, valve 214 may be opened to allow insufflation fluid to flow through a source of insufflation fluid 216 through elongate tubular member 212 and into body cavity BC. Once body cavity BC has been insufflated, surgical instrument 16 may be inserted through reducer bore 208 in reducer seal 206 and into body cavity BC to perform surgical operations therein.

Figure 17:
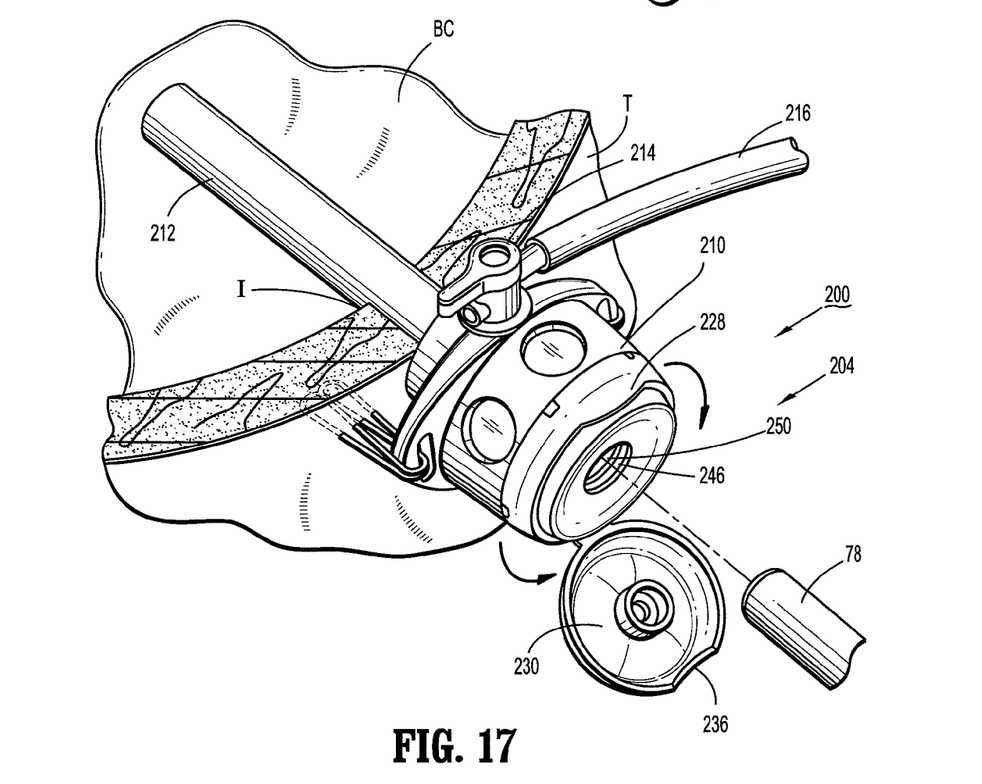
FIG. 17 is a perspective view similar to FIG. 14 with the reducer cap pivoted out of alignment with a seal of the cannula.

Referring to FIG. 17, when a larger diameter surgical instrument, such as, for example surgical instrument 78 is needed to perform surgical procedures within body cavity BC, protrusion 236 on second circumferential portion 230 may be manipulated to move or pivot second circumferential portion 230 away from first circumferential portion 228 of reducer cap 204. Thereafter, surgical instrument 78 may be inserted through the larger diameter seal opening 250 formed in cannula seal 246 and passed into body cavity BC so as to perform additional surgical procedures. As noted hereinabove, reducer cap 204 is rotatable relative to cannula body 210 so as to orient second circumferential portion 230 away from valve 214.

Thus, it can be seen that restyled flip-top cannula 200 provides the advantages of having a rotatable reducer cap 204, relatively large concave portions 234 and 260 for guiding various diameter surgical instruments towards the disclosed seals as well as providing integrated suture ears for securing restyled flip top cannula 200 to tissue.

Figure 18:
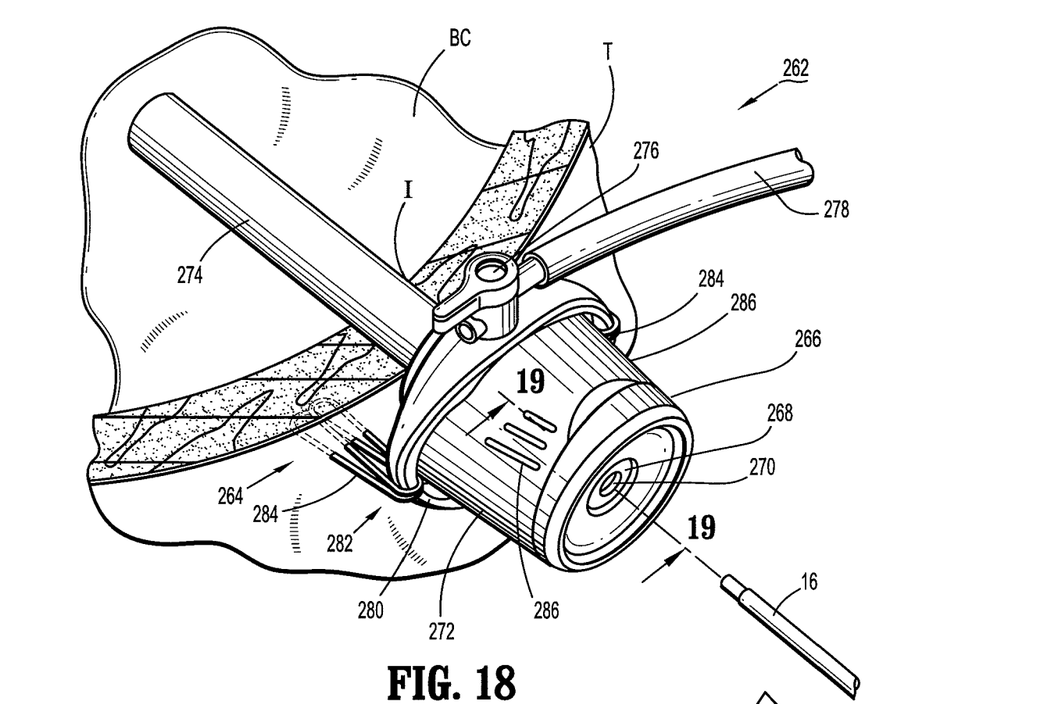
FIG. 18 is a perspective view of yet a further embodiment of a cannula incorporating an integrated, flip-top reducer cap

Referring now to FIGS. 18 through 21, and initially with regard to FIG. 18, there is disclosed an integrated flip-top cannula 262 for use with various diameter surgical instruments. Integrated flip-top cannula 262 generally includes a cannula 264 having an integrated reducer cap 266. Reducer cap 266 includes a reducer seal 268 having a reducer bore 270 for receipt of surgical instruments therethrough.

Cannula 264 includes a cannula body 272 having an elongate tubular member 274 extending distally there from. Cannula 264 additionally includes a valve 276 connected to a source of insufflation fluid 278 for insufflating body cavity BC. Suture ears 280 are formed about cannula body toward 72 and are provided to facilitate guiding a surgical needle (not shown) towards suture holes 282 to facilitate securing integrated flip top cannula 262 to tissue T with sutures 284 and a manner similar to that described with respect to prior embodiments hereinabove. Ribs 286 are provided about cannula body 272 to facilitate manipulating integrated flip top cannula 262 through tissue T.

Figure 19:
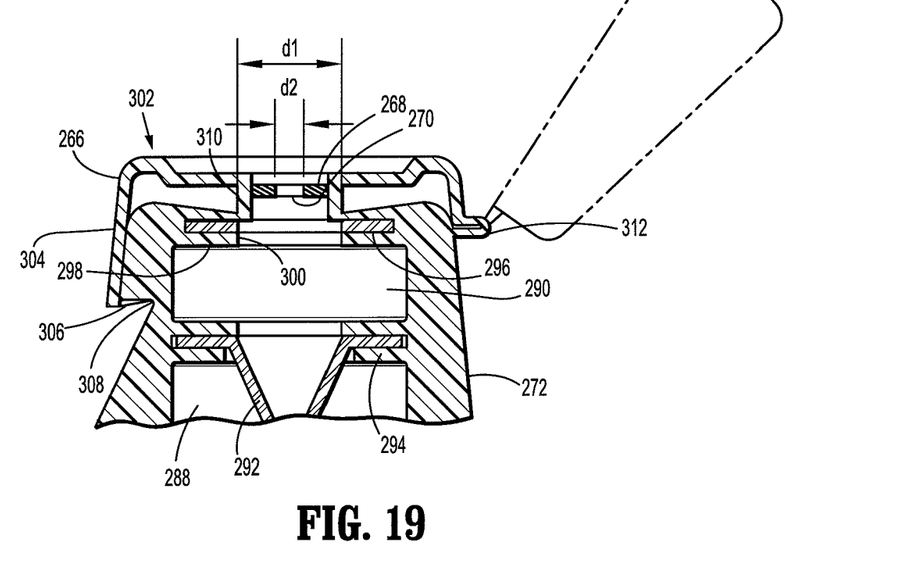
FIG. 19 is a side sectional view taken along line 19-19 of FIG. 18.

Referring to FIG. 19, cannula body 272 generally includes a first inner chamber 288 and a second inner chamber 290. First and second inner chambers 288 and 290, respectively, are separated by a duckbill valve 292. Duckbill valve 292 is supported within cannula body 272 by a flange 294. Cannula seal 296 defines a seal opening 300 having a predetermined diameter d1 for receipt of surgical instruments having a diameter larger than that of surgical instrument 16.

Reducer cap 266 is generally asymmetric and includes an upper dished portion 302 surrounding reducer seal 268. Reducer cap 266 further includes a generally elongated depending side portion 304 which terminates in an inwardly directed flexible catch 306. Flexible catch 306 is configured to engage and undercut side 308 formed in cannula body 272 to secure a reducer cap 266 a closed position adjacent cannula body 272. As shown, a downwardly projecting circular portion 310 extends distally from dished portion 302 two seal against cannula seal 296 when reducer cap 266 is in the closed position. As shown, reducer bore 270 of reducer seal 268 as a predetermined diameter d2 which is configured to receive surgical instruments such as, for example, surgical instrument 16. Diameter d2 of reducer seal 268 is smaller than diameter d1 of cannula seal 296.

Figure 20:
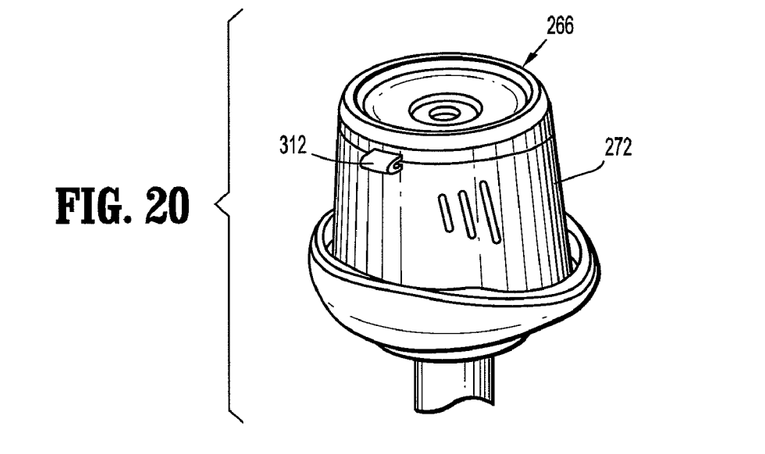
FIG. 20 is a perspective view of the embodiment of FIG. 18 with the reducer cap in position on the body of the cannula.

Referring now to FIGS. 19 and 20, integrated flip-top cannula 262 differs from the previously disclosed embodiments in that reducer cap 266 is formed integrally with cannula body 272. Specifically, a portion of cannula body 272 is formed with a living hinge 312 which is integral with reducer cap 266. Reducer cap 266 is movable from a closed position wherein flexible catch 306 is engaged with undercut 308 formed in cannula body 272 to an open position wherein reducer cap 266 is spaced apart approximately of 135° from cannula seal 296. While not specifically shown, living hinge 312 may incorporate a detents mechanism to hold reducer cap 266 in the open position. Alternatively, living hinge 312 may be molded such that in an unstressed position it holds reducer cap 266 in the open position similar to those embodiments describe hereinabove.

Referring to FIG. 18, in use, integrated flip-top cannula 262 is manipulated to insert elongated tubular member 274 through incision I in tissue T such that elongated tubular member 274 is positioned within body cavity BC. Similar to those procedures describe hereinabove, valve 276 is manipulated to cause insufflation fluid to flow through source of insufflation fluid 278 and into body cavity BC. Thereafter, a surgical needle (not shown) is manipulated along suture ears 280 and through suture holes 282 to secure integrated flip top cannula 262 to tissue T with sutures 284. Surgical instrument 16 may now be inserted through reducer bore 270 in reducer seal 268 and pass into body cavity BC so as to perform various surgical procedures.

Figure 21:
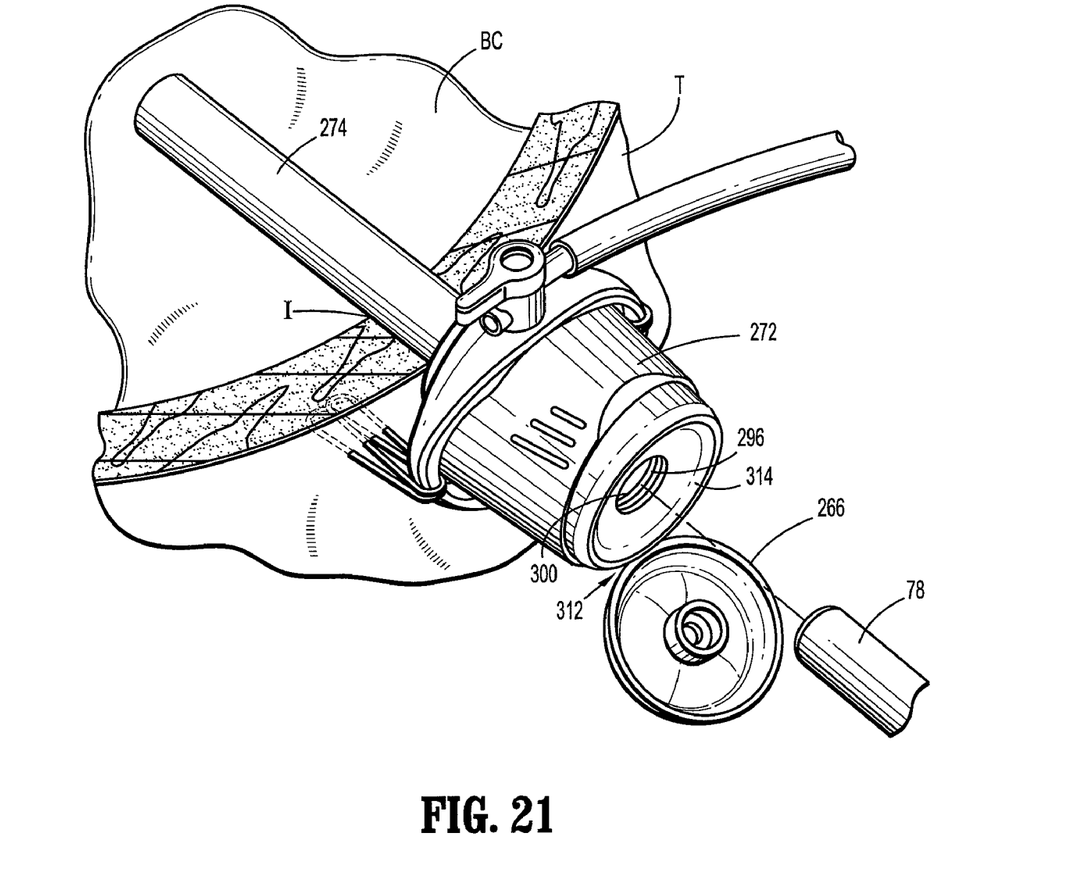
FIG. 21 is a perspective view similar to FIG. 18 with the reducer cap pivoted out of alignment with a seal of the cannula.

As best shown in FIG. 21, when the use of a larger diameter surgical instrument, such as, for example, surgical instrument 78 is desired flexible catch 306 may be drawn away from undercut 308 in cannula body 272 to allow reducer cap 266 to be pivoted about hinge 312 and moved to the open position exposing cannula seal 296. It should be noted that cannula body 272 may incorporate a slightly concave portion 314 to facilitate guiding surgical instrument 78 toward seal opening 300 in cannula seal 296. Once positioned through integrated flip top cannula 262, surgical instrument 78 may be utilized to perform various additional surgical procedures.

Thus, it can be appreciated, that in this embodiment, by providing reducer cap 266 integrally with cannula body 272 the amount of components included in integrated flip top cannula 262 is reduced.

It will be understood that various modifications may be made to the embodiments disclosed herein. For example, the disclosed embodiments may incorporate various types of detent mechanisms to maintain the disclosed reducer caps in the open position relative to the cannula body. Further, the disclosed reducer caps may be formed entirely or partially of a flexible, elastomeric material. Additionally, the disclosed cannula bodies may incorporate various sealing structure other than duckbill valves or no internal sealing structure at all. Still further, other methods of securing the cannula body to a tissue may be provided, such as, for example, adhesives, stapling, etc. Therefore, the above description should not be construed as limiting, but merely as exemplifications of particular embodiments. Those skilled in the art will envision other modifications within the scope and spirit of the claims appended hereto.

The invention claimed is:

1. A flip-top cannula comprising:
a cannula having a cannula body defining an inner chamber, an elongate tubular member extending distally from the cannula body and a cannula seal positioned on a proximal end of the cannula body, the cannula seal having an opening of a first predetermined diameter for receipt of a first surgical instrument, the proximal end of the cannula body including a recess; and
a reducer cap including a reducer seal defining a bore having a second predetermined diameter for receipt of a second surgical instrument, the second predetermined diameter being less than the first predetermined diameter, the reducer cap including a first portion circumferentially surrounding the proximal end of the cannula body, a second portion movably mounted relative to the first portion and a flexible hinge connecting the first and second portions, the second portion including a top surface and a circumferential side surface, the circumferential side surface including an inner lip, wherein the second portion is movable from a closed position wherein the inner lip engages the recess in the proximal end of the cannula body such that the reducer seal overlies the cannula seal to an open position wherein the inner lip disengages the recess in the proximal end of the cannula body such that the reducer seal is spaced from the cannula seal.

2. The flip-top cannula as recited in claim 1, wherein the flexible hinge is integral with the first and second portions.

3. The flip-top cannula as recited in claim 1, wherein the reducer cap is formed of an elastomeric material.

4. The flip-top cannula as recited in claim 3, wherein the flexible hinge is molded to hold the second portion in an open position of approximately 135° relative to the first portion when the flexible hinge is in an unstressed condition.

5. The flip-top cannula as recited in claim 1, wherein the top surface of the second portion engages a proximal face of the cannula body and the circumferential side surface of the second portion circumferentially surrounds the proximal end of the cannula body when the second portion is in the closed position.

6. The flip-top cannula as recited in claim 5, wherein the first portion is rotatable around the cannula body.

7. The flip-top cannula as recited in claim 1, wherein the second portion includes a concave portion surrounding the reducer seal such that the concave portion guides a surgical instrument towards the reducer seal.

8. The flip-top cannula as recited in claim 1, wherein the first portion includes a plurality of nubs to facilitate grasping the cannula.

9. The flip-top cannula as recited in claim 1, wherein the cannula body includes a suture flange defining a suture hole for receipt of suture material to secure the cannula relative to tissue.

10. The flip-top cannula as recited in claim 1, wherein the cannula body includes at least one projection having a groove for receipt of suture material.

11. A flip-top cannula comprising:
a cannula having a cannula body defining an inner chamber, an elongate tubular member extending distally from the cannula body and a cannula seal positioned on a proximal end of the cannula body, the cannula seal having an opening of a first predetermined diameter for receipt of a first surgical instrument, the cannula body including an undercut side; and
a reducer cap formed integrally with the cannula body and including a reducer seal defining a bore having a second predetermined diameter for receipt of a second surgical instrument, the second predetermined diameter being less than the first predetermined diameter, the reducer cap including a top surface and a circumferential side surface configured to circumferentially surround the proximal end of the cannula body, the circumferential side surface including an elongated side portion with an inwardly directed catch, wherein the reducer cap is movable from a closed position wherein the inwardly directed catch is engaged with the undercut side of the cannula body to an open position wherein the inwardly directed catch is disengaged from the undercut side of the cannula body.

12. The flip-top cannula as recited in claim 11, further including a flexible, living hinge integrally formed between the cannula and the reducer cap.

13. The flip-top cannula as recited in claim 11, wherein the cannula body includes a channel having at least one suture hole, the channel directing a surgical needle having suture material towards the at least one suture hole.

14. The flip-top cannula as recited in claim 11, wherein the reducer cap is asymmetric such that the elongated side portion and its opposite portion on the circumferential side surface are asymmetric with respect to a longitudinal axis of the cannula.

15. A flip-top cannula comprising:
a cannula having a cannula body defining an inner chamber, an elongate tubular member extending distally from the cannula body and a cannula seal positioned on a proximal end of the cannula body, the cannula seal having an opening of a first predetermined diameter for receipt of a first surgical instrument, the proximal end of the cannula body including a recess; and
a reducer cap including a reducer seal defining a bore having a second predetermined diameter for receipt of a second surgical instrument, the second predetermined diameter being less than the first predetermined diameter, the reducer cap including a first portion circumferentially surrounding the proximal end of the cannula body, the first portion including an inner lip configured to engage the recess in the proximal end of the cannula body, the reducer cap further including a second portion movably mounted relative to the first portion and a flexible hinge connecting the first and second portions, the second portion including a top surface and a circumferential side surface, wherein the second portion is movable from a closed position wherein the top surface of the second portion engages a proximal face of the cannula body and the circumferential side surface of the second portion circumferentially surrounds the proximal end of the cannula body to an open position wherein the second portion is spaced away from the cannula body.

16. The flip-top cannula as recited in claim 7, wherein the cannula body includes a concave portion adjacent the cannula seal provided to seal against the concave portion of the reducer cap surrounding the reducer seal.

17. The flip-top cannula as recited in claim 1, wherein the second portion of the reducer cap includes a tab facilitating moving the second portion between the closed and open positions.

18. The flip-top cannula as recited in claim 15, wherein the second portion of the reducer cap includes a downward projection surrounding the reducer seal such that the downward projection seals against the cannula seal when the reducer cap is in the closed position.

19. The flip-top cannula as recited in claim 15, wherein the first portion of the reducer cap includes cut outs facilitating rotating the reducer cap around the cannula body.

* * * * *